US010786420B2

(12) United States Patent
FitzPatrick et al.

(10) Patent No.: US 10,786,420 B2
(45) Date of Patent: Sep. 29, 2020

(54) MOBILITY ASSISTING WALKER DEVICE (71) Applicant: Avenue Mobility Ltd, Stamford, CT (US)

(72) Inventors: Helen Ix FitzPatrick, Greenwich, CT (US); Geri W. Roper, Greenwich, CT (US); Kenneth A Tarlow, San Rafael, CA (US)

(73) Assignee: AVENUE MOBILITY LTD., Stamford, CT (US)

( * ) Notice: Subject to any disclaimer, the term of this patent is extended or adjusted under 35 U.S.C. 154(b) by 0 days.

(21) Appl. No.: 16/367,986

(22) Filed: Mar. 28, 2019

(65) Prior Publication Data

US 2019/0298602 A1 Oct. 3, 2019

Related U.S. Application Data

(60) Provisional application No. 62/649,650, filed on Mar. 29, 2018.

(51) Int. Cl.
*A61H 3/04* (2006.01)
*A61B 5/11* (2006.01)

(52) U.S. Cl.
CPC .............. *A61H 3/04* (2013.01); *A61B 5/112* (2013.01); *A61B 2562/0223* (2013.01); *A61H 2201/0161* (2013.01); *A61H 2201/1635* (2013.01); *A61H 2201/5043* (2013.01)

(58) Field of Classification Search
CPC ........................................................ B62B 3/02
See application file for complete search history.

(56) References Cited

U.S. PATENT DOCUMENTS

| 7,306,246 B2 * | 12/2007 | Gale | A61H 3/04 |
| | | | 280/47.34 |
| 8,695,616 B2 * | 4/2014 | Huggins | A45B 1/00 |
| | | | 135/66 |
| 2015/0274187 A1 * | 10/2015 | Storch | B62B 7/042 |
| | | | 280/47.38 |
| 2018/0242888 A1 * | 8/2018 | Schmutzer | G06F 19/3481 |

* cited by examiner

*Primary Examiner* — James A Shriver, II
*Assistant Examiner* — James J Triggs
(74) *Attorney, Agent, or Firm* — Wissing Miller LLP (57) ABSTRACT

A mobility assisting walker device with a folding frame assembly, a pair of non-swiveling wheels, a pair of friction pads, a pair of support handles and a pair of lift arms is disclosed. The non-swivel wheels are mounted to the bottom front portion of the folding frame and the friction pads mounted to the bottom rear portion of the frame. The support handles are mounted to the top portion of the frame assembly. The lift arms are each attached to the outer slidable juncture of the frame. The folding frame assembly is capable of going from a narrow, storage position to a wide use position by a user raising or lowering the lift arms. The frame assembly configured to allow the user to have maximum stride capability while using the walker device. A preferred embodiment includes the friction pads are constructed from injection molded high sticktion TPE plastic.

11 Claims, 8 Drawing Sheets

MOBILITY ASSISTING WALKER DEVICE

CROSS REFERENCE TO RELATED APPLICATIONS

This application claims priority under 35 U.S.C. § 119 to U.S. Provisional Patent Application No. 62/649,650, filed on Mar. 29, 2018. The disclosure of that application is incorporated herein by reference.

FIELD OF THE INVENTION

This invention relates generally to the field of mobility walkers and more specifically to a folding mobility assisting walker device.

BACKGROUND

Mobility assisting walkers have been available for many years. They are used by people who need extra support while walking. They generally consist of a metal frame where the lower section terminates in two front wheels and two rear facing friction feet, and the upper section terminates in a pair of support handles.

Various forms of folding frames have been designed for walkers so that they may be stored in a compact form for transport or home storage. One type of folding frame is designed to cause the left and right frame members to be drawn inward. This configuration can be helpful when the user needs to pass through narrow spaces because the distance between the left side and right side can be decreased as needed. however, some current side to side folding models cannot safely remain in a narrow configuration during use because when the user puts downward pressure on the hand grips, the entire frame assembly tends to spread apart. Additionally, the construction of current side to side folding models includes positioning of structural elements which can impede the user's stride and therefore interfere with full mobility during use. Finally, the friction feet of some walkers may wear out quickly and need replacing. Additionally, the friction feet may not have an optimal amount of sticktion needed for control of the walker during use.

SUMMARY

One primary object of the disclosure is to provide a mobility assisting walker device that folds into a compact upright assembly.

Another object of the disclosure is to provide a mobility assisting walker device that allows the user to have freedom of walking motion while using the device.

Another object of the disclosure is to provide a mobility assisting walker device that employs friction inducing pads to improve control of the forward motion of the walker when in use.

A further object of the disclosure is to provide a mobility assisting walker that includes forward facing LED aimable lights mounted to each handle grip.

Other objects and advantages of the present disclosure will become apparent from the following descriptions, taken in connection with the accompanying drawings, wherein, by way of illustration and example, an embodiment of the present invention is disclosed.

In accordance with a preferred embodiment, there is disclosed a mobility assisting walker device comprising: a folding frame assembly, a pair of non-swiveling wheels, a pair of friction pads, a pair of support handles, a pair of lift arms, said non-swivel wheels mounted to the bottom front portion of said folding frame assembly, said friction pads mounted to the bottom rear portion of said folding frame assembly, said pair of support handles mounted to the top portion of said folding frame assembly, said lift arms each attached to the outer slidable juncture of said folding frame assembly, said folding frame assembly capable of going from a narrow, storage position to a wide use position by a user raising or lowering said lift arms, and said frame assembly configured without a structural member that would interfere with a user's stride capability while using said walker device.

BRIEF DESCRIPTION OF THE DRAWINGS

The drawings constitute a part of this specification and include exemplary embodiments to the invention, which may be embodied in various forms. It is to be understood that in some instances various aspects of the disclosure may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
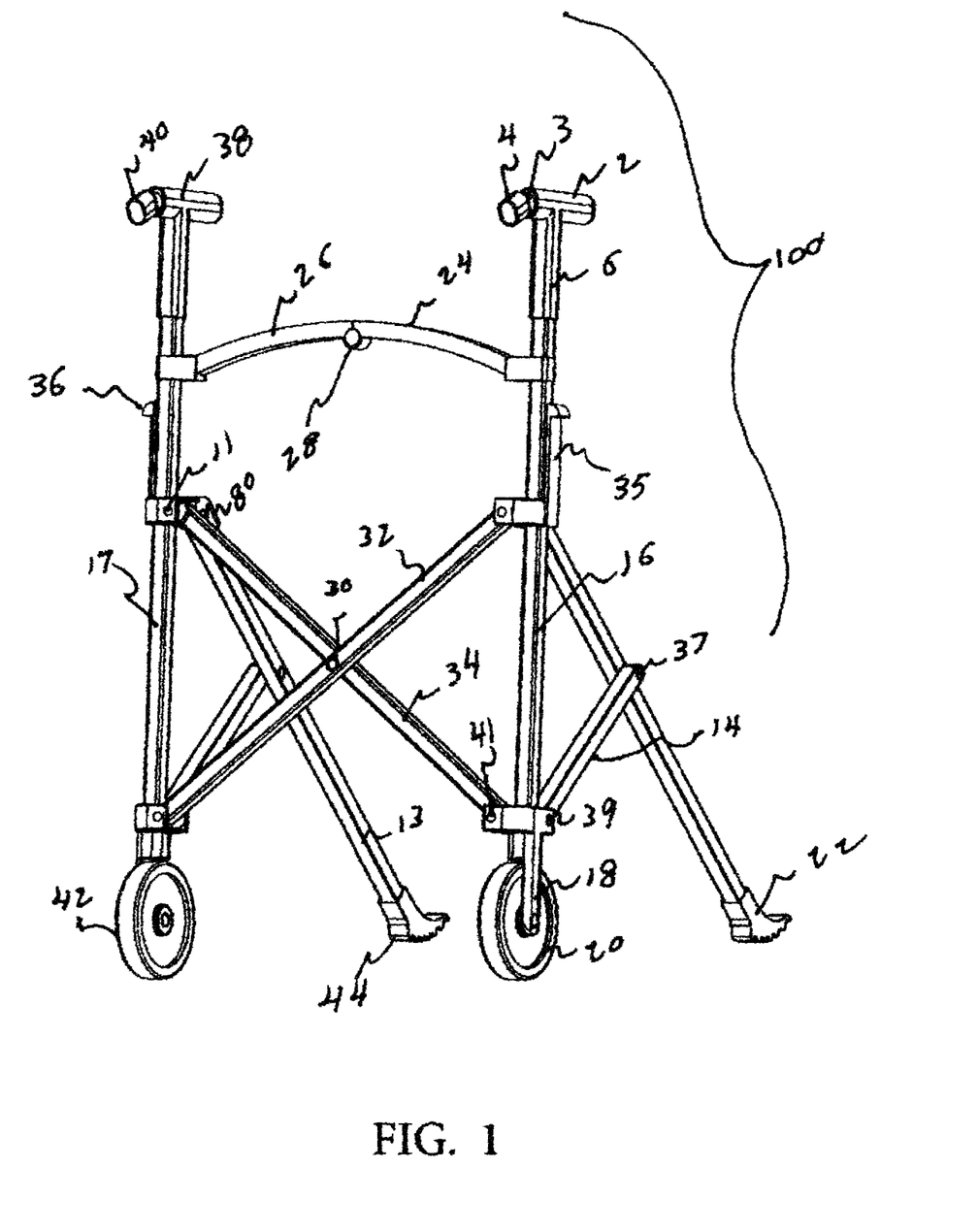
FIG. 1 is a perspective view of an embodiment of the disclosure.

Referring now to FIG. 1 we see a perspective view of a walker 100. A folding frame assembly is made up of vertical members 16 and 17, cross members 32, 34, rear leg members 12, 13, side connector members 14 and hinged side to side members 24, 26. The frame components on one side are mirror images of the opposite side. Therefore, for purposes of simplicity, in some cases, only the right-side frame members have been numbered. Rear leg members 12, 13 terminate in friction inducing pads 22, 44 that are injection molded from high stiction TPE (Thermoplastic Elastomer) plastic. The feet 22,44 include a bottom tread that maintains a secure frictional force as the user rolls the walker 100 forward to provide control and stability during operation. Vertical members 16 terminate in wheel holders 18 which support non-swivel wheels 20, 42. Side to side members 24, 26 are arched and hinged so that the user does not have to pull up on the pieces 24, 26 when compressing the frame for storage or for passing through a narrow area.

To compress the frame, the user pulls up on lift handles 35, 36 which cause sliding connectors 10, 11 to rise and cross members 32, 34 to fold in on each other. This process causes rear leg members 12, 13 to automatically draw in to vertical members 16 via brace members 14. The upper portion of vertical members 16 terminate in height adjustable handles 2, 38 which have aimable LED lights 4, 40 extending from the front of each handle. Pin joints such as those connected with elements 10, 11, 30, 37, 39, 41 act as fulcrum points to allow the frame members to fold into each other when needed.

Figure 2:
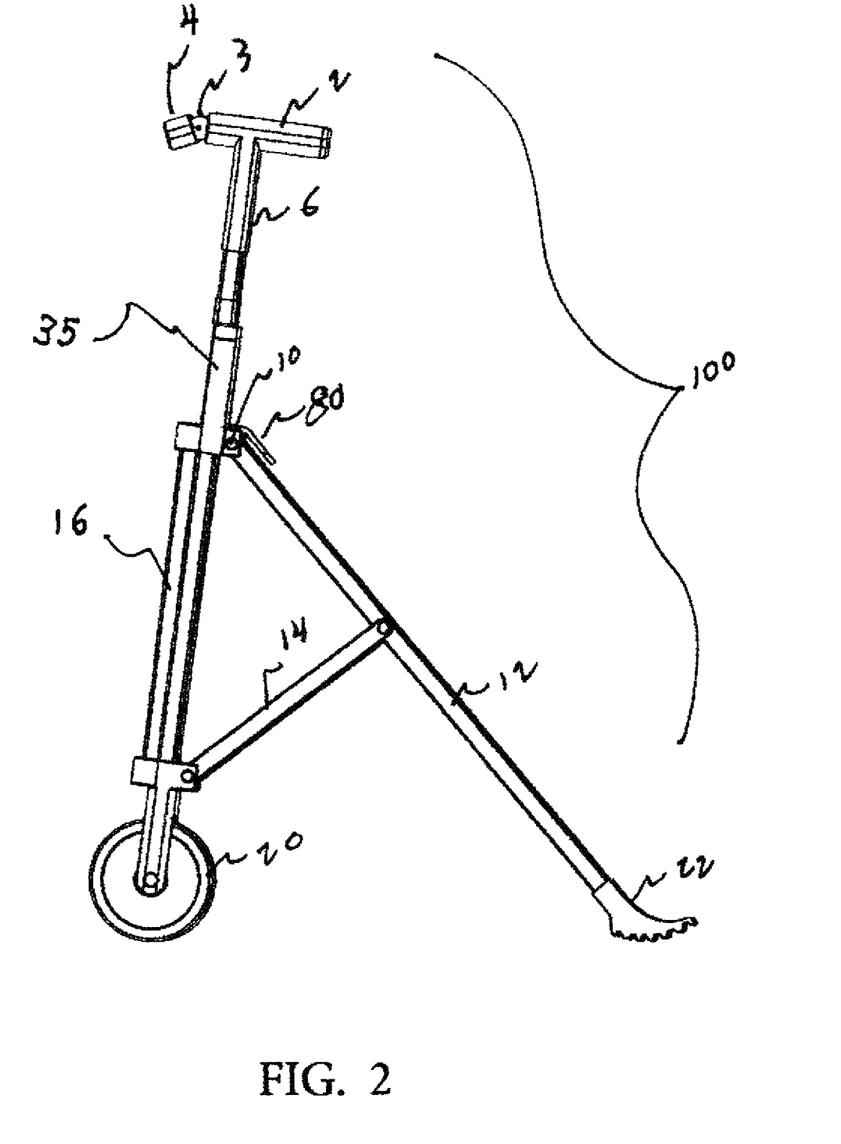
FIG. 2 is a side view of an embodiment of FIG. 1.

FIG. 2 is a side view of the walker 100 showing the relationship between the front leg 16 and rear leg 12. The tread pattern on foot 22 can also clearly be seen. The frictional hinge 3 on handle allows the LED light 4 to be set at a desired angle. Pedometer housing 80 can be seen attached to frame member 13 as shown in detail in FIG. 7.

Figure 3:
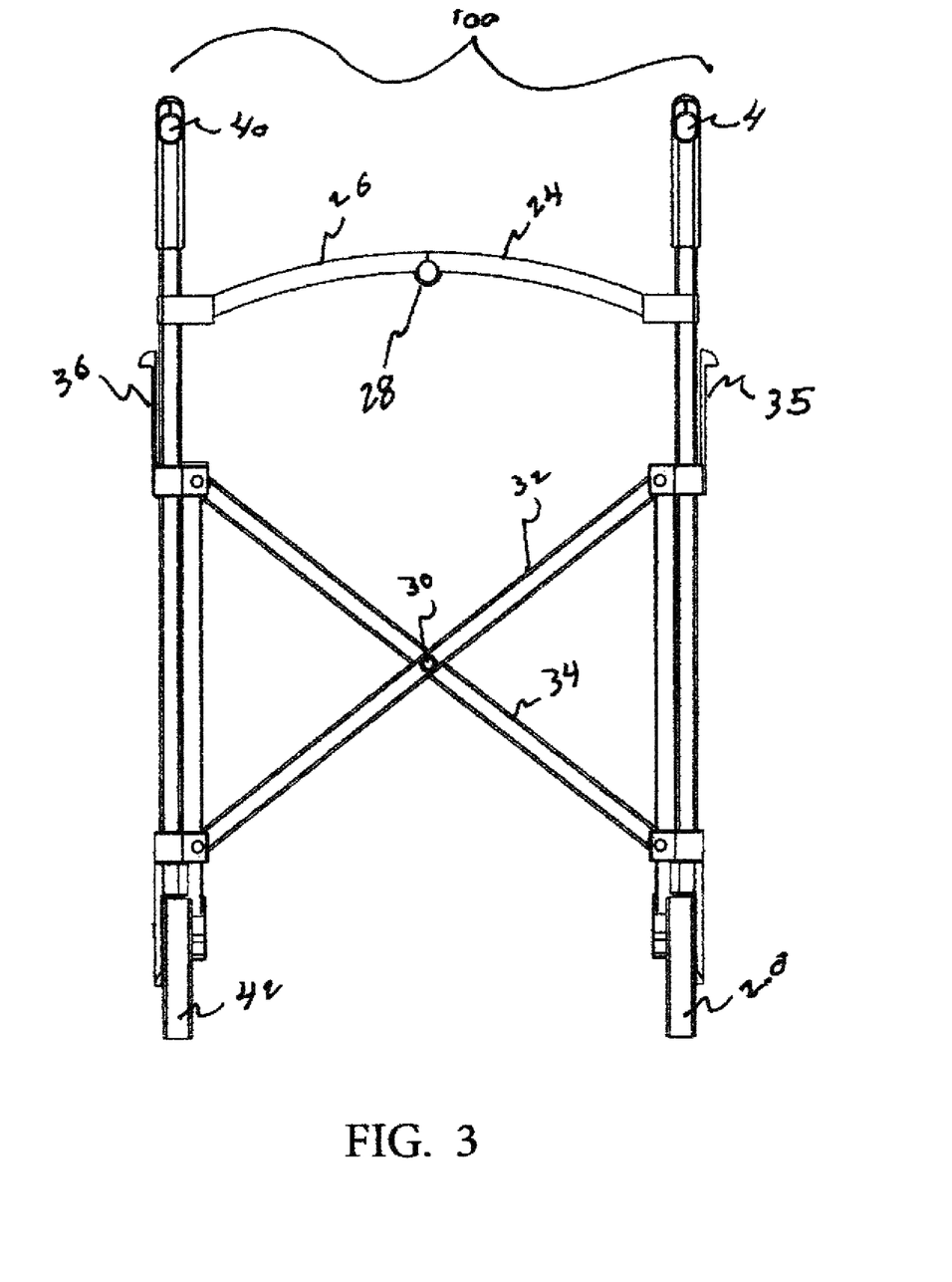
FIG. 3 is a front view of an embodiment of FIG. 1.

FIG. 3 is a front view of the walker 100 in the fully open position.

Figure 4:
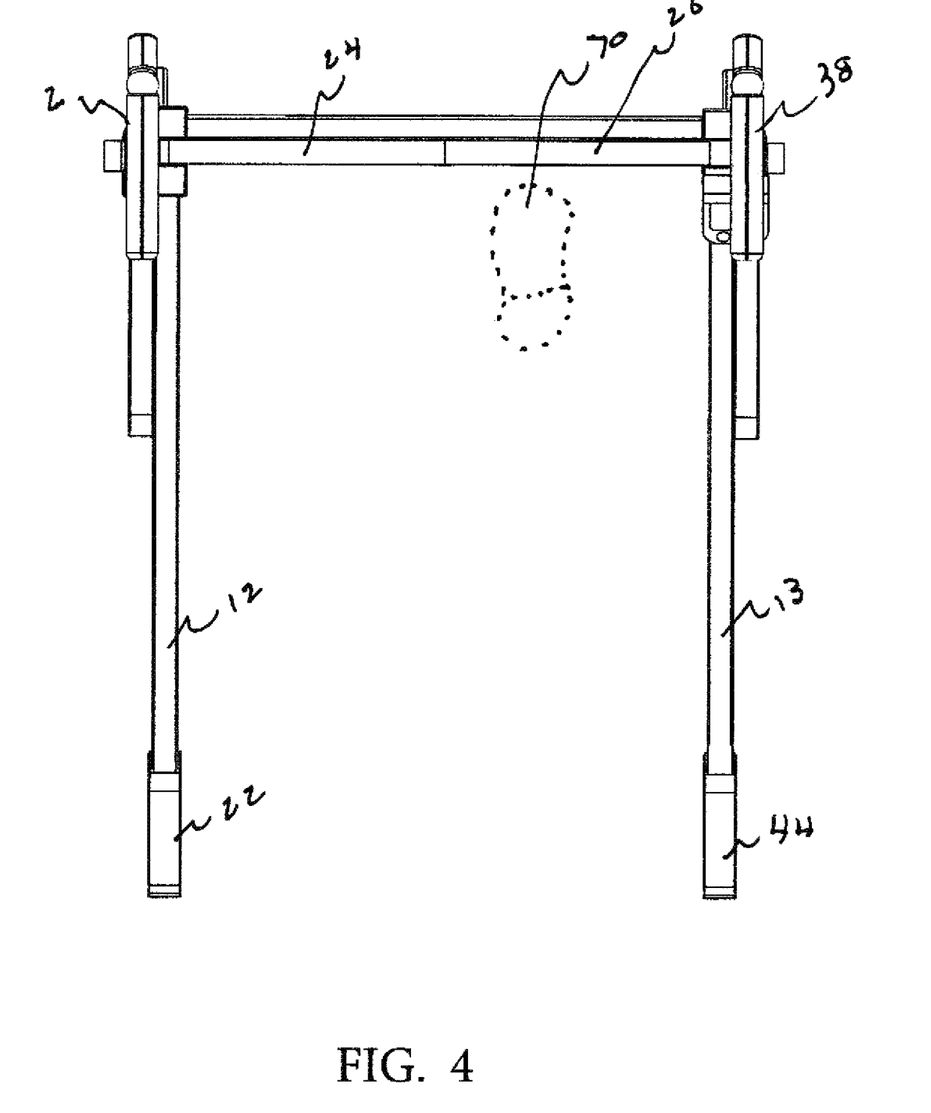
FIG. 4 is a top view of an embodiment of FIG. 1.

FIG. 4 is a top view of the walker 100 showing that there are no structural members between sides behind cross members 32, 34 that would interfere with the user's stride as shown by dotted line foot print 70.

Figure 5:
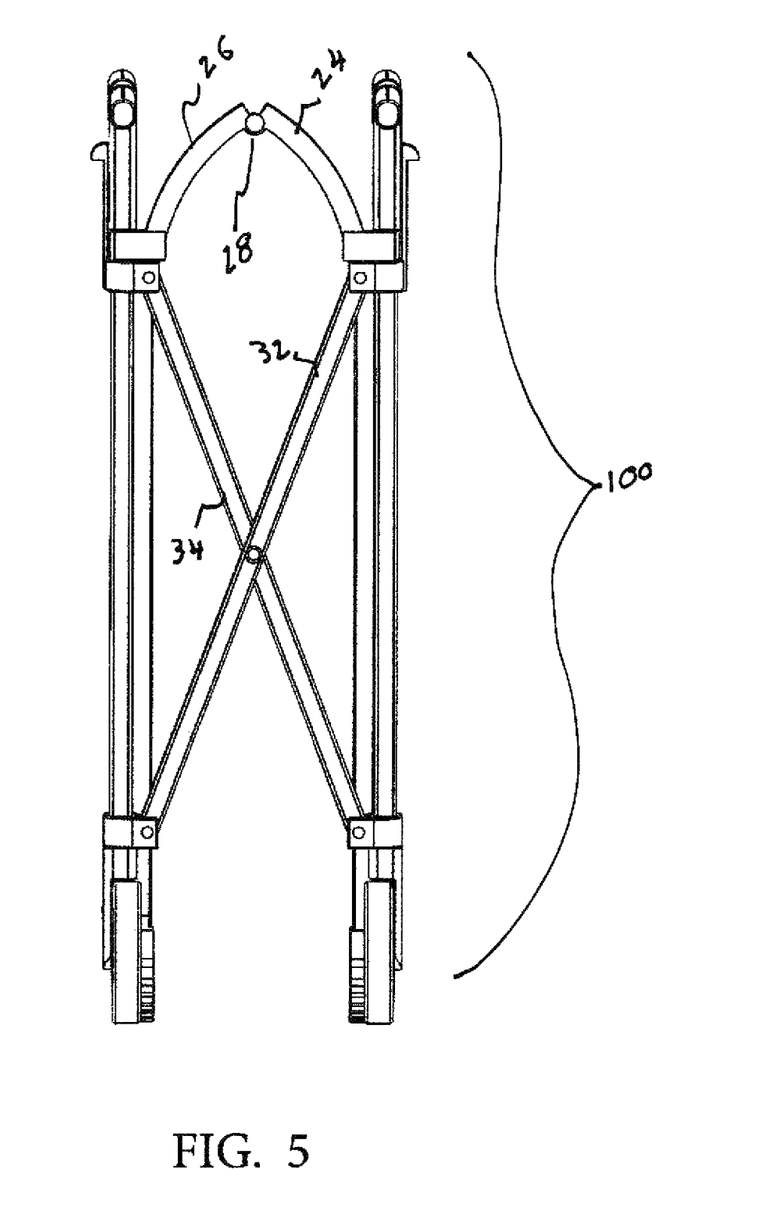
FIG. 5 is a front view of a partially compressed view of an embodiment of FIG. 1.

FIG. 5 is a front view of the walker 100 in the partially open position. This orientation is helpful when the user needs to pass through a narrow space. The mechanical configuration of the folding frame assembly is such that the frame maintains its state of width in a stable fashion even when the user places weight and pressure on the handles 2, 38.

Figure 6:
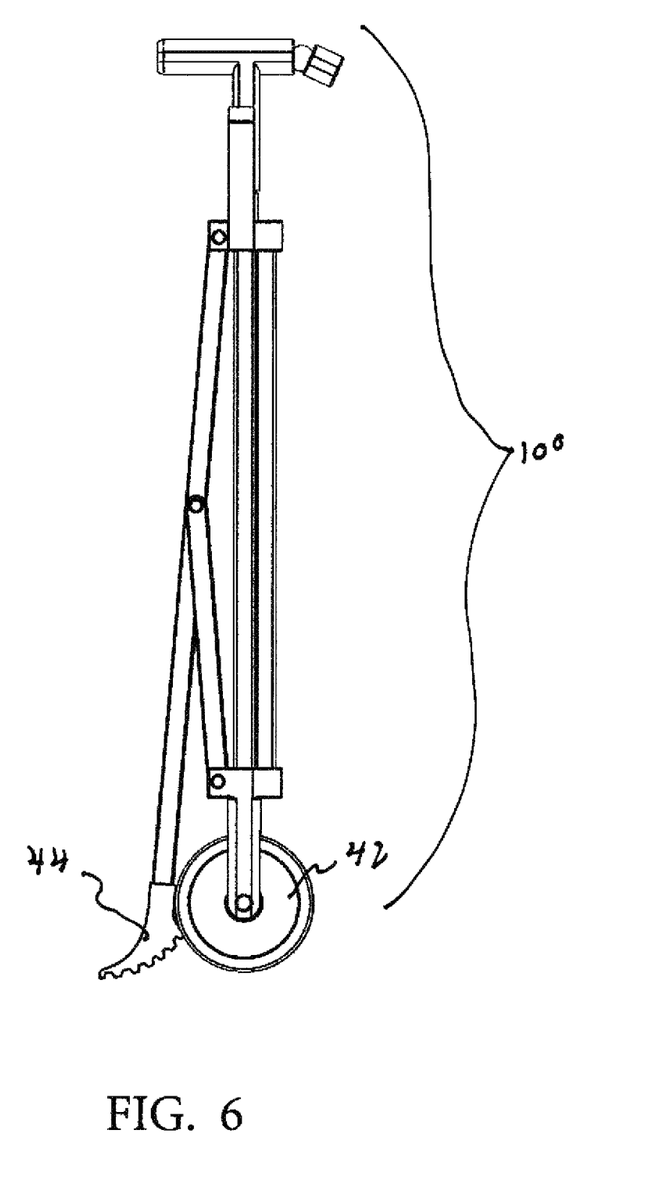
FIG. 6 is a side view of a fully compressed view of an embodiment of FIG. 1.

FIG. 6 is a side view of the walker 100 in the fully closed condition which is compact and which allows the entire unit 100 to stand upright without assistance while in the closed position.

Figure 7:
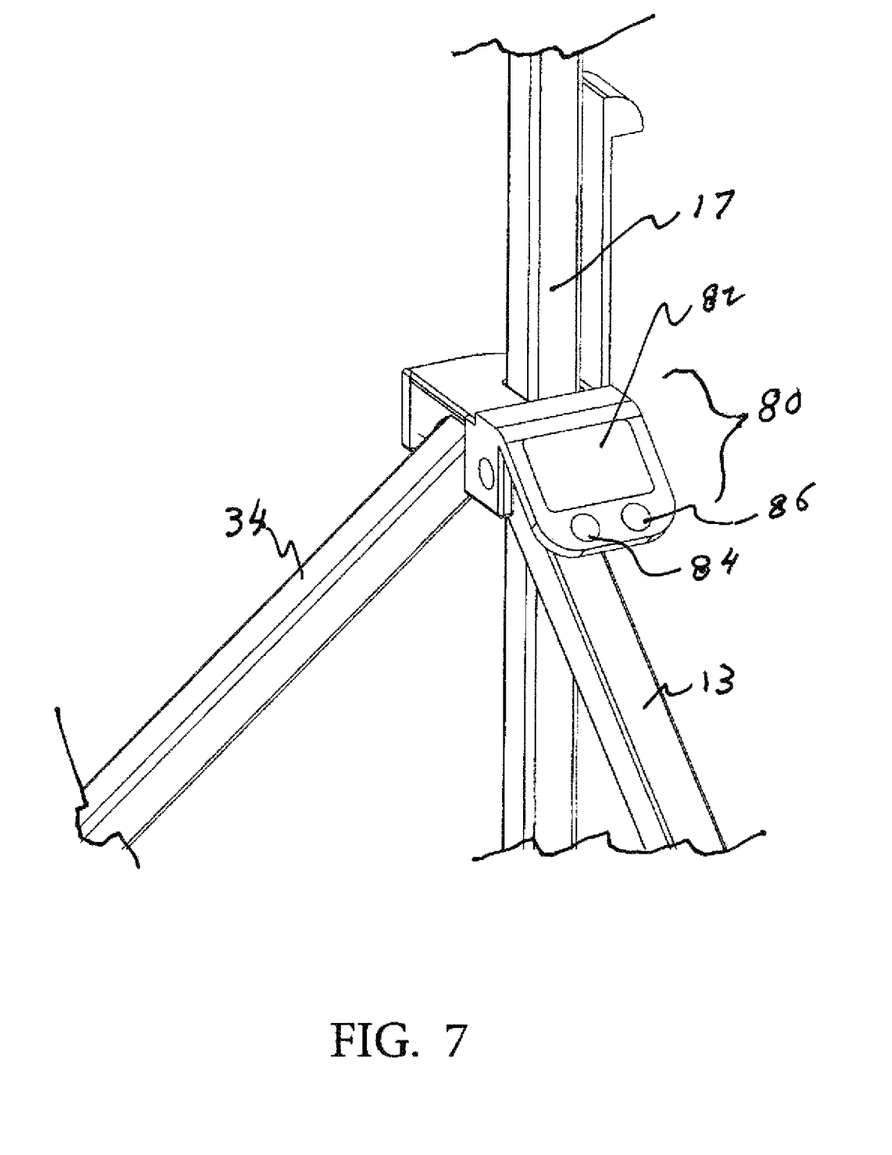
FIG. 7 is a partial perspective view of the pedometer portion of an embodiment of FIG. 1.

FIG. 7 is a partial perspective view showing a pedometer assembly 80 attached to the frame member 13. The pedometer assembly includes a digital display 82 showing distance traveled and on-off button 84. The user can also press button 86 to see calories burned.

Figure 8:
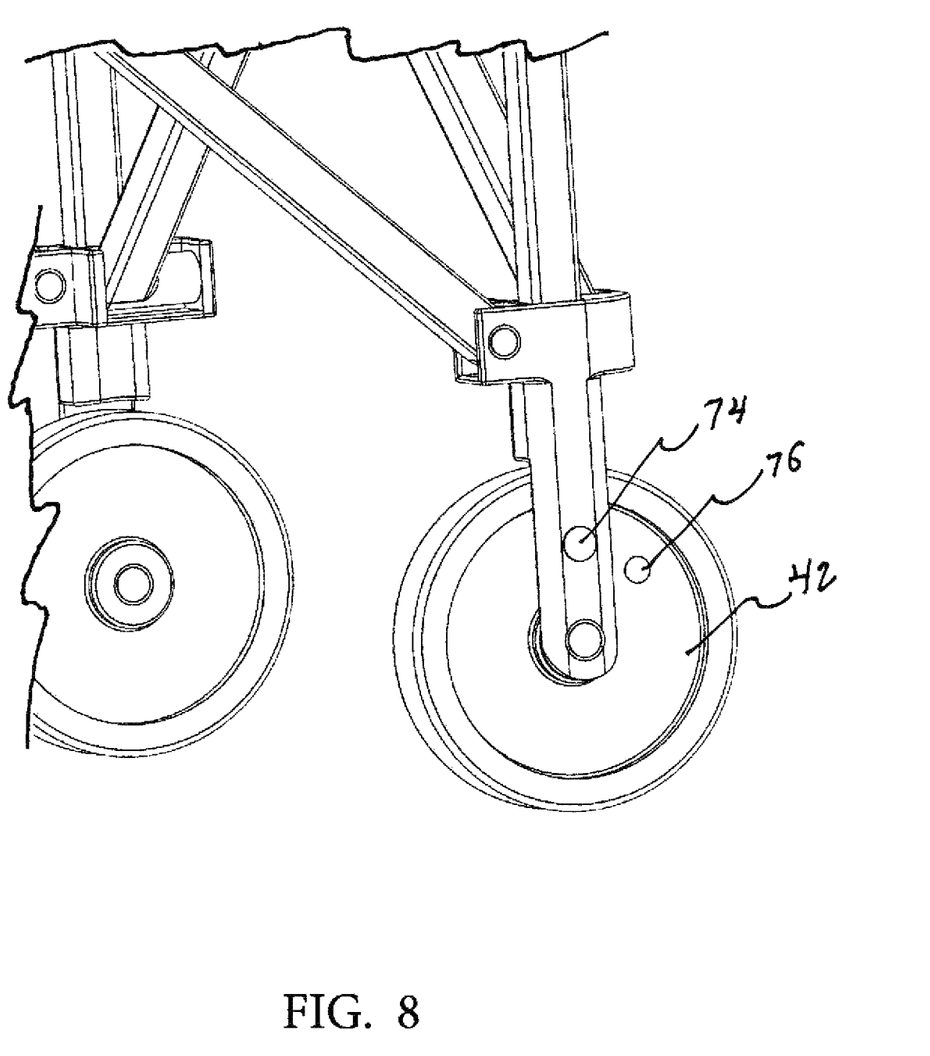
FIG. 8 is a partial perspective view of the wheel magnet and reed switch.

FIG. 8 is a partial perspective view showing a magnet 76 mounted to wheel 42 and a reed switch 74 mounted to the wheel frame so that every time the magnet 76 passes the reed switch 74, one revolution is recorded and this information is sent via cable, not shown, to the pedometer assembly 80.

The mobility assisting walker device of the present invention 100 is preferably made from light-weight materials such as aluminum or carbon fiber but may also be made from heavier materials such as tubular steel. The present invention 100 is designed to support a person weighing as much as five hundred pounds.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A mobility assisting walker device comprising:
a folding frame assembly;
one or more wheels rotatably mounted to a bottom front portion of the frame assembly;
one or more friction pads mounted to a bottom rear portion of the frame assembly;
one or more support handles mounted to a top portion of the frame assembly; and
one or more lift handles slidably coupled with the frame assembly, wherein sliding the lift handles in a first direction folds the folding frame assembly from a narrow, storage position toward a wide use position and sliding the lift handles in a second direction folds the frame assembly from the wide use position toward the narrow storage position, wherein the folding frame assembly comprises an upper horizontally biased frame portion, wherein the biased frame portion is arched and hinged, and wherein the biased frame portion folds toward the narrow storage position when the lift handles are moved in the second direction.

2. The device of claim 1, wherein the folding frame assembly comprises a pair of side frames connected together by one or more cantilevered supports, wherein the lift handles are fixed to respective ones of the cantilevered supports and wherein movement of the lift handles in the first direction causes the cantilevered supports to move the side frames from the narrow storage position toward the wide use position.

3. The device of claim 2, wherein the side frames and cantilevered supports are positioned outside of a rearward facing open region, the open region configured to allow a user to stride in a forward direction.

4. The device of claim 2, wherein the cantilevered supports comprise two shafts rotatably connected at their midportion, wherein a first end of each shaft is connected with a respective one of the lift handles and a second end of each shaft is rotatably connected with one of the side frames, wherein the second direction is upward, and wherein moving the lift handles upward causes the shafts to fold toward one another.

5. The device of claim 4, wherein the frame further comprises one or more rear leg assemblies, wherein the friction pads are mounted at bottom ends of the rear leg assemblies and wherein the rear leg assemblies are connected with the cantilevered supports and adapted to fold rearward from the side frames when the lift handles are moved in the first direction.

6. The device of claim 1, wherein said friction pads are constructed from a polymer.

7. The device of claim 6, wherein the polymer is a thermoplastic elastomer.

8. The device of claim 1 further comprising one or more lights movably mounted on respective ones of the support handles.

9. The device of claim 1 further comprising a pedometer assembly mounted to said folding frame assembly.

10. The device of claim 9, wherein the pedometer assembly comprises a reed switch mounted to the lower portion of the frame and a magnetic element mounted to the wheel, wherein rotation of the magnetic element past the reed switch indicates a distance traversed by the user.

11. The device of claim 10, wherein the pedometer assembly comprises an electronic assembly connected with the reed switch, the electronic assembly comprising an LED display, wherein the electronic assembly monitors a signal from the reed switch, calculates the distance traversed, and displays an indication of the distance on the display.

* * * * *